(12) United States Patent
Yano et al.

(10) Patent No.: US 6,818,614 B2
(45) Date of Patent: Nov. 16, 2004

(54) COMPOUNDS HAVING ANTIFUNGAL ACTIVITY

(75) Inventors: Tatsuya Yano, Tokyo (JP); Masatoshi Inukai, Matsudo (JP); Toshio Takatsu, Nishitokyo (JP); Isshin Tanaka, Tsukuba (JP)

(73) Assignee: Sankyo Company, Limited, Tokyo (JP)

( * ) Notice: Subject to any disclaimer, the term of this patent is extended or adjusted under 35 U.S.C. 154(b) by 228 days.

(21) Appl. No.: 10/087,633

(22) Filed: Mar. 1, 2002

(65) Prior Publication Data

US 2002/0160946 A1 Oct. 31, 2002

Related U.S. Application Data

(63) Continuation-in-part of application No. PCT/JP00/05937, filed on Aug. 31, 2000.

(30) Foreign Application Priority Data

Sep. 3, 1999 (JP) ............................................. 11-249959

(51) Int. Cl.[7] ........................ A61K 38/12; A61K 38/16; C12P 21/04
(52) U.S. Cl. ............................ 514/9; 435/71.3; 530/317
(58) Field of Search ........................ 435/71.3; 530/317; 514/9

(56) References Cited

FOREIGN PATENT DOCUMENTS

| JP | 4-316578 | 6/1992 |
|---|---|---|
| JP | 10-45662 | 2/1998 |

OTHER PUBLICATIONS

The Merck Manual, General Medicine. Berkow, R., ed., 1987, vol. I, 15th Edition (Merck Sharp & Dohme Research Labs.: Rahway, NJ), pp. 108–110.*
P. Venkatasubbaiah, C.G. Van Dyke and W.S. Chilton, "Phytotoxic Metabolites of *Phoma sorghina*, a New Foliar Pathogen of Pokeweed", *Mycologia*, 84 (5), pp. 715–723 (1992).

D.M. Schmatz, G. Abruzo, M.A. Powles, D.C. McFadden, J.M. Balkovec, R.M. Black, K. Nollstadt and K. Bartizal. "Pneumocandins From *Zalerion arboricola*", *The Journal of Antibiotics*, 45, 1886–1891 (1992).
Robert Nyfeler and Walter Keller–Schierlen, "Stoffwechselproduke von Mikroorganismen", *Helvetica Chimica Acta*, 57, 2459–2477 (1974).
Katsushige Ikai, Katzutoh Takesako, Kazuro Shiomi, Makoto Moriguchi, Yoshihisa Umeda, Junko Yamamoto and Ikunoshin Kato, "Structure of Aureobasidin A", *The Journal of Antibiotics*, 44, 925–933 (1991).
P. Venkatasubbaiah, C.G. Van Dyke and W.S. Chilton, "Phytotoxic Metabolites of *Phoma sorghin*, A New Foliar Pathogen of Pokeweed", *Mycologia*, 84, 715–723 (1992).

* cited by examiner

*Primary Examiner*—Jean C. Witz
*Assistant Examiner*—Susan Hanley May
(74) *Attorney, Agent, or Firm*—Frishauf, Holtz, Goodman & Chick, P.C.

(57) ABSTRACT

A compound of the following chemical structure (I) which exhibits antifungal activity and is useful in treating and preventing fungal infectious diseases:

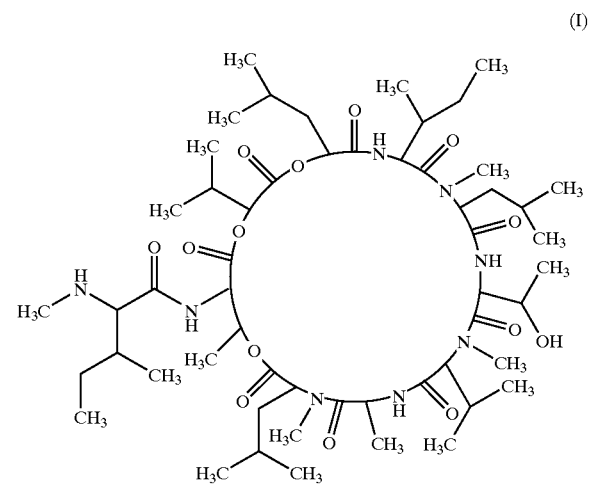

32 Claims, No Drawings

COMPOUNDS HAVING ANTIFUNGAL ACTIVITY

CROSS REFERENCE TO RELATED APPLICATION

This application is a continuation-in-part application of International Application PCT/JP00/05937 filed on Aug. 31, 2000 (not published in English), the entire contents of which are incorporated by reference herein.

BACKGROUND OF THE INVENTION

1. Field of the Invention

The present invention relates to novel compounds having antifungal activity; to a process for preparation of said compounds, comprising isolation of said compounds from the fermentation product of a microorganism producing said compounds; to medicaments containing said compounds as an active ingredient; to pharmaceutical compositions containing said compounds as an active ingredient; to therapeutic or prophylactic agents for fungal infectious diseases containing said compounds as an active ingredient; to a microorganism producing said compounds; to uses of said compounds; and to methods for treating or preventing fungal infectious diseases, comprising administering a pharmaceutically effective amount of said compounds to an animal.

2. Background Information

At the present time, amphotericin B, flucytosine and azole derivatives are clinically used as antifungal agents. Some of these compounds have begun become to exhibit some problems, such as the emergence of cytotoxicity, and of fungi resistant to these compounds.

It has been disclosed that some microorganisms produce antifungal compounds. For example, Zalerion genus produces pneumocandins (Schmatz, D. M., et al., J. Antibiotics 45, 1886(1992)), *Aspergillus* genus produces echinocandins (Nyfeler, R. and Keller-Schierlein, W., Helv. Chim. Acta 57, 2459(1974)) and *Aureobasidium* genus produces *aureobasidins* (Ikai, K., et al., J. Antibiotics, 44, 925(1991)). However, these have not been clinically used yet.

SUMMARY OF THE INVENTION

The inventors have found novel compounds having antifungal activity in fermentation products of a microorganism, *Phoma* sp. SANK 13899 strain, that was obtained from a soil sample collected in Chichi-island, Ogasawara-mura, Tokyo.

The present invention provides novel compounds having antifungal activity; a process for preparation of said compounds; medicaments containing said compounds as an active ingredient; pharmaceutical compositions containing said compounds as an active ingredient; therapeutic or prophylactic agents for fungal infectious diseases containing said compounds as an active ingredient; a microorganism producing said compounds; uses of said compounds; and methods for treating or preventing fungal infectious diseases comprising administering an effective amount of said compounds to an animal.

(1) The present invention includes a new antifungal compound of the following chemical structure (I), or a salt thereof.

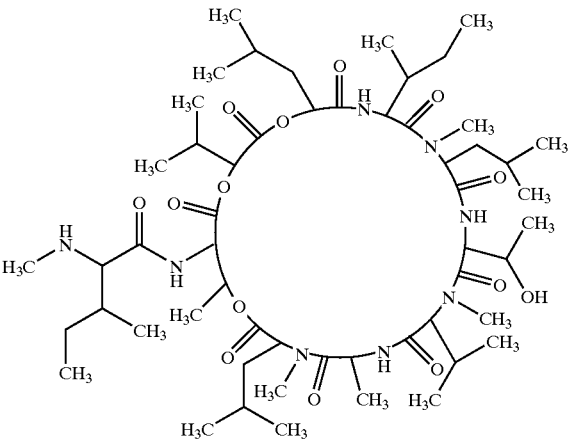

(I)

(2) The present invention includes a compound having the following physicochemical properties, or a salt thereof:

1) Property: Basic liposoluble powder
2) Molecular formula: $C_{55}H_{98}N_8O_{14}$
3) Molecular weight: 1094 (FAB-MS method)
4) High resolution FAB-MS $[M+H]^+$
   calculated for $C_{55}H_{99}N_8O_{14}$ 1095.7281
   found 1095.7365
5) Ultra violet absorption spectrum: End absorption
6) Infra red absorption spectrum (KBr pellet, $cm^{-1}$): 3434, 3335, 2962, 2937, 2875, 2806, 1750, 1684, 1641, 1509, 1469, 1412, 1371, 1314, 1294, 1271, 1204, 1156, 1128, 1074, 1020
7) Optical rotation: $[\alpha]_D^{25}$ −120° (c 1.0, methanol)
8) $^1$H NMR spectrum (in $CDCl_3$, 500 MHz, δ (ppm), internal standard: tetramethylsilane) 0.78(3H), 0.79 (3H), 0.80(3H), 0.82(3H), 0.87(3H), 0.88(1H), 0.92 (3H), 0.94(3H), 0.96(3H), 0.97(3H), 0.98(3H), 1.01 (3H), 1.02(3H), 1.03(3H), 1.06(3H), 1.21(1H), 1.41 (3H), 1.41(1H), 1.48(1H), 1.48(1H), 1.49(1H), 1.52 (3H), 1.55(1H), 1.65(1H), 1.66(1H), 1.70(2H), 1.73 (1H), 1.81(1H), 1.87(1H), 2.28(1H), 2.31(1H), 2.37 (1H), 2.48(3H), 2.89(3H), 2.94(3H), 2.96(1H), 3.29 (3H), 3.56(1H), 4.06(1H), 4.14(1H), 4.77(1H), 4.78 (1H), 4.84(1H), 4.91(1H), 4.96(1H), 5.21(1H), 5.25 (1H), 5.53(1H), 6.39(1H), 7.83(1H), 7.94(1H), 8.28 (1H)
9) $^{13}$C NMR spectrum (in $CDCl_3$, 500 MHz, δ (ppm), internal standard: tetramethylsilane): 10.9(q), 11.9(q), 15.0(q), 15.1(q), 16.0(q), 16.6(q), 17.4(q), 18.3(q), 18.6 (q), 18.7(q), 19.1(q), 21.0(q), 21.4(q), 22.1(q), 23.1(q), 23.51(q), 23.54(q), 24.2(t), 24.6(d), 24.8(d), 25.4(d), 25.5(t), 27.7(d), 29.5(q), 29.8(d), 30.2(q), 36.1(q), 36.5 (t), 37.7(t), 38.8(d), 38.4(d), 39.7(t), 40.9(q), 46.2(d), 51.8(d), 53.1(d), 54.7(d), 55.1(d), 63.9(d), 64.7(d), 68.1 (d), 70.1(d), 73.4(d), 74.3(d), 77.1(d), 169.03(s), 169.04(s), 169.6(s), 169.8(s), 169.9(s), 170.3(s), 172.0 (s), 173.4(s), 173.8(s), 174.0(s)
10) High performance liquid chromatography:
    Column: SHODEX ASAHIPAK C8P 50 4E (4.6 mm (diameter)×250 mm (length); product of Showa Denko K.K.)
    Mobile phase: acetonitrile: 10 mM aqueous ammonium hydrogencarbonate solution=13:7

Flow rate: 0.7 ml/minute
Wavelength of detection: λ210 nm
Retention time: 10.20 minutes 11) Solubility: Soluble in dimethylsulfoxide, methanol, and chloroform
12) Amino acid analysis: Threonine, alanine and isoleucine were detected from the hydrolysate.

(3) The present invention includes a new antifungal compound of the following chemical structure (II).

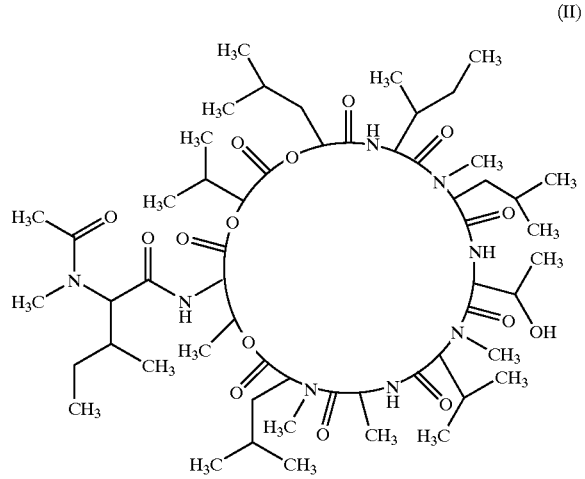

(II)

(4) The present invention includes a compound having the following physicochemical properties:

1) Property: Neutral liposoluble powder
2) Molecular formula: $C_{57}H_{100}N_8O_{15}$
3) Molecular weight: 1136 (FAB-MS method)
4) High resolution FAB-MS $[M+H]^+$
   calculated for $C_{57}H_{101}N_8O_{15}$ 1137.7387
   found 1137.7410
5) Ultra violet absorption spectrum: End absorption
6) Infra red absorption spectrum (KBr pellet, $cm^{-1}$): 3433, 3333, 2963, 2937, 2875, 1751, 1686, 1642, 1516, 1469, 1409, 1388, 1372, 1311, 1292, 1272, 1201, 1156, 1128, 1074, 1017
7) Optical rotation: $[\alpha]_D^{25}$ −131° (c 1.0, methanol)
8) $^1$H NMR spectrum (in $CDCl_3$, 500 MHz, δ (ppm), internal standard: tetramethylsilane): 0.78(3H), 0.79 (3H), 0.80(3H), 0.83(3H), 0.87(1H), 0.87(3H), 0.90 (3H), 0.92(3H), 0.93(3H), 0.95(3H), 0.95(3H), 0.98 (3H), 0.98(3H), 1.01(3H), 1.01(3H), 1.03(1H), 1.05 (3H), 1.28(3H), 1.37(1H), 1.40(1H), 1.46(1H), 1.47 (1H), 1.49(1H), 1.51(3H), 1.64(1H), 1.65(1H), 1.66 (1H), 1.86(1H), 1.72(1H), 1.78(1H), 2.12(3H), 2.13 (1H), 2.26(1H), 2.31(1H), 2.37(1H), 2.88(3H), 2.93 (3H), 2.97(3H), 3.28(3H), 3.56(1H), 4.03(1H), 4.15 (3H), 4.73(1H), 4.78(3H), 4.82(1H), 4.83(1H), 4.91 (1H), 4.97(1H), 5.15(1H), 5.28(1H), 5.50(1H), 6.37 (1H), 6.87(1H), 7.86(1H), 8.29(1H)
9) $^{13}$C NMR spectrum (in $CDCl_3$, 500 MHz, δ (ppm), internal: tetramethylsilane): 10.5(q), 10.9(q), 14.9(q), 15.1(q), 15.6(q), 16.6(q), 16.7(q), 18.3(q), 18.7(q), 19.0 (q), 20.8(q), 21.4(q), 22.0(q), 22.1(q), 23.1(q), 23.6(q), 23.6(q), 24.1(t), 24.6(t), 24.7(d) 24.8(d), 25.4(d), 27.7 (d), 29.5(q), 29.8(d), 30.2(d), 31.6(d), 31.8(q), 36.1(t), 37.6(t), 38.4(d) 39.6(t), 40.9(q), 46.1(d), 51.8(d), 53.1 (d), 54.7(d), 54.7(d), 61.2(d), 63.9(d), 64.6(d), 68.1(d) 73.1(d), 74.3(d), 77.0(d), 168.9(s), 168.9(s), 169.1(s), 169.9(s), 169.9(s), 170.3(s), 170.6(s), 171.7(s) 172.0 (s), 173.3(s), 173.8(s)
10) High performance liquid chromatography:
   Column: SHODEX ASAHIPAK C8P 50 4E (4.6 mm (diameter)×250 mm (length); product of Showa Denko K.K.)
   Mobile phase: acetonitrile: 10 mM aqueous ammonium hydrogencarbonate solution=13:7
   Flow rate: 0.7 ml/minute
   Wave length of detection: A 210 nm
   Retention time: 9.05 minutes (5) The present invention includes a process for preparing a compound according to any of (1) to (4), comprising fermentating a microorganism that belongs to *Phoma* genus and produces a compound according to any of (1) to (4), and isolating a compound according to any of (1) to (4) from the fermentation product of said microorganism.

(6) The present invention includes a process according to (5) wherein the microorganism that belongs to *Phoma* genus and produces a compound according to any of (1) to (4) is *Phoma* sp. SANK 13899 (FERM BP-6851) strain.

(7) The present invention includes a medicament containing a compound according to any of (1) to (4) or a salt thereof as an active ingredient.

(8) The present invention includes a therapeutic or prophylactic agent for fungal infectious diseases containing a compound according to any of (1) to (4) or a salt thereof as an active ingredient.

(9) The present invention includes *Phoma* sp. SANK 13899 (FERM BP-6851) strain.

(10) The present invention includes uses of a compound according to any of (1) to (4) or a salt thereof.

(11) The present invention includes a method for treating or preventing a fungal infection, comprising administering a pharmaceutically effective amount of a compound according to any of (1) to (4) or a salt thereof to an animal.

(12) In addition, the present invention includes a pharmaceutical composition containing a compound according to any of (1) to (4) or a salt thereof as an active ingredient.

The compounds of the present invention are the compounds described in (1) to (4). Among these compounds, the compounds described in (1) and (3) have the following general chemical structure:

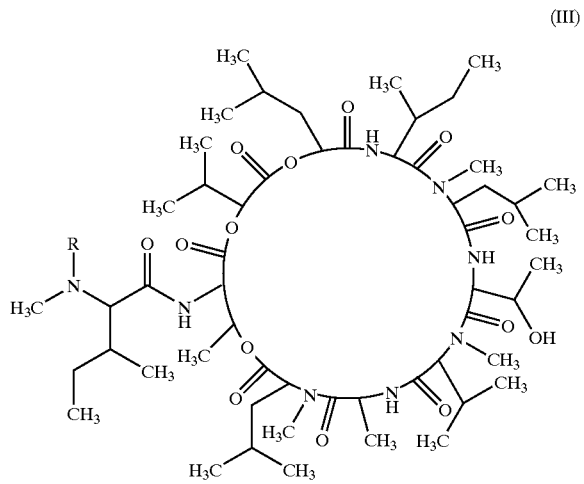

(III)

wherein R is a hydrogen or $COCH_3$. In this invention, the compounds of general chemical structure (III) are referred to as F-15078. The compound described in (1) is the compound of general chemical structure (III) wherein R is hydrogen. In this invention, the compound described in (1) or the compound having the physicochemical properties described in (2) is referred to as F-15078A. The compound described in (3) is the compound of general chemical structure (III) wherein R is $COCH_3$. The compound described in (3) or the compound having the physicochemical properties described in (4) is referred to as F15078B.

DETAILED DESCRIPTION OF THE INVENTION

F-15078A can be converted into a salt thereof by conventional techniques. Salts of F-15078A can be applied to any use, for example, medical use and veterinary use. When applied to medical use and/or veterinary use, there is no limitation provided that the salts are pharmaceutically acceptable. Examples of such salts include inorganic salts such as hydrochloride and organic salts such as pamoic acid salt. When applied to other uses, for example, as intermediates in organic synthesis, there is no limitation to the salts. Examples of such salts include inorganic salts such as acetate, bromide, chloride, hydrochloride, hydrobromide, iodide, sulfate, phosphate and diphosphate; and organic acid salts such as citrate, maleate, pamoic acid salt and tartarate and so forth.

Each compound F-15078 can possess various isomers; however these isomers are represented as the same chemical structure. The present invention includes each of the individual isomers and also includes mixtures thereof.

Certain compounds F-15078 form a solvate (for example hydrate) and the present invention includes said solvates. For example, when allowed to stand in the air or when recrystallized, certain compounds F-15078 absorb or attach water to form a hydrate. The present invention encompasses said hydrates.

The present invention includes prodrugs that are converted into the parent compound F-15078 in the body.

F-15078 producing microorganism

F-15078 can be obtained from fermentation products of fungi producing said compounds. Microorganisms producing F-15078 are fungi that belong to *Phoma* genus and preferably the microorganism is *Phoma* sp. SANK 13899 strain (herein after referred to SANK 13899 strain). SANK 13899 strain was isolated from soil collected in Chichi-island, Ogasawara-mura, Tokyo.

SANK 13899 strain was cultivated in the following culture media in order to observe the morphological properties thereof. The composition of each medium is described below.

| PDA medium (Potato Dextrose Agar medium) | |
|---|---|
| Nissui Potato Dextrose Agar (product of Nissui Pharmaceutical Co., Ltd.) | 39 g |
| Distilled water | 1000 ml |
| CMA medium (Corn Meal Agar medium) | |
| Corn Meal Agar (product of Nissui Pharmaceutical Co., Ltd.) | 17 g |
| Distilled water | 1000 ml |
| WSH medium | |
| Quaker oatmeal | 10 g |
| Magnesium sulfate heptahydrate | 1 g |
| Potassium dihydrogen phosphate | 1 g |
| Sodium nitrate | 1 g |

| -continued | |
|---|---|
| Agar | 20 g |
| Distilled water | 1000 ml |
| Miura's medium | |
| Glucose | 1 g |
| Potassium dihydrogen phosphate | 1 g |
| Magnesium sulfate heptahydrate | 0.2 g |
| Potassium chloride | 0.2 g |
| Yeast extract | 0.2 g |
| Sodium nitrate | 2 g |
| Agar | 20 g |
| Distilled water | 1000 ml |
| CYA medium (Czapek Yeast Extract Agar medium) | |
| Dipotassium hydrogen phosphate | 2 g |
| Concentrated Czapek solution* | 10 ml |
| Yeast extract | 5 g |
| Sucrose | 30 g |
| Agar | 15 g |
| Distilled water | 1000 ml |
| MEA medium (Malt Extract Nutrient Agar medium) | |
| Malt extract | 20 g |
| Peptone | 1 g |
| Glucose | 20 g |
| Agar | 20 g |
| Distilled water | 1000 ml |
| G25N medium (25% Glycerol Nitrate Agar medium) | |
| Dipotassium hydrogen phosphate | 0.75 g |
| Concentrated Czapek solution* | 7.5 ml |
| Yeast extract | 3.7 g |
| Glycerol | 250 g |
| Agar | 12 g |
| Distilled water | 750 ml |
| *The composition of concentrated Czapek solution is as follows: | |
| Sodium nitrate | 30 g |
| Potassium chloride | 5 g |
| Magnesium sulfate heptahydrate | 5 g |
| Iron (II) sulfate heptahydrate | 0.1 g |
| Zinc sulfate heptahydrate | 0.1 g |
| Copper sulfate pentahydrate | 0.05 g |
| Distilled water | 100 ml |

Color tone was determined according to the Methuen Handbook of Colour (Komerup, A. and Wanscher, J. H. (1978) (3rd. edition). Erye Methuen, London).

The morphological properties of SANK 13899 strain under cultivation are as follows:

The growth of SANK 13899 strain on PAD medium at 23° C. after two weeks is from 13 to 17 mm in diameter. The colony has a fluffy cotton appearance, the center of the colony rises and has a fluffy wool appearance and the edge of the colony has a slightly tooth-like appearance. The surface color of the colony is from gray (3B1) to white and the reverse color is brown (from 6E5 to 4).

The growth of SANK 13899 strain on CMA medium at 23° C. after two weeks is from 15 to 17 mm in diameter. The colony has a powdery appearance and the edge of the colony has a tooth-like appearance. The surface color of the colony is from grayish green (27E5) to dull green (27E4) and the reverse color is dark green (27F4).

The growth of SANK 13899 strain on Miura's medium at 23° C. after two weeks is from 22 to 33 mm in diameter. The colony is flat and the edge of the colony is clear. The surface color of the colony is white and the reverse color is from yellowish white (3A2) to white.

The growth of SANK 13899 strain on WSH medium at 23° C. after two weeks is from 33 to 34 mm in diameter. The colony is flat and the edge of the colony is smooth. The surface color of the colony is from pale yellow (3A3) to yellowish white (3A2) and the reverse color is the same as that of the surface.

The growth of SANK 13899 strain on CYA medium at 23° C. after two weeks is from 34 to 35 mm in diameter. The colony has a fluffy cotton appearance, the center of the colony rises and has a fluffy wool appearance, and secretes soluble pale-color pigment. The edge of the colony is flat and smooth. The surface color of the colony is from grayish orange (6B3) and the reverse color is from brownish orange (6C3) to brown (6D8).

The growth of SANK 13899 strain on MEA medium at 23° C. after two weeks is from 15 to 23 mm in diameter. The colony has a fluffy cotton appearance, the center of the colony rises and has a fluffy wool appearance. The edge of the colony is flat and has an appearance from smooth to slightly tooth-like. The surface color of the colony is from white to gray (3B 1) and the reverse color is dark green (from 28F4 to 3).

The hypha is from 0.5 to 3 $\mu$g in diameter and frequently forms hypha1 cord and has thin or thick cell walls. The surface of the mycelium is smooth or rough and the color is from colorless to brown.

When cultivated on ODA medium, Miura's medium and the like for more than 1 month, SANK 13899 strain forms a sector and forms pycnidia which are embedded in the agar of the sector region.

The morphological properties of the pycnidium are as follows:

The diameter of the pycnidium was from 100 to 200 $\mu$m. The pycnidium was embedded or partially embedded in the agar, was spherical or near-spherical, and was brown or black. Any opening part thereof was not observed. The cells forming conidia were from 7.5 to 9 $\mu$m×from 1.3 to 1.8 $\mu$m and were formed on the cells forming the spherical pycnidium. The cells were single cell and cylindrical or pen point shape and colorless. The phialo conidium was from 3.5 to 4.7 $\mu$m×from 1.3 to 1.8 $\mu$m and was cylindrical, single cell and colorless. The hypha was from 0.5 to 3 $\mu$m in diameter and frequently formed hypha1 cord and had thin or thick cell walls. The surface of the mycelium was smooth or rough and was from colorless to brown. SANK 13899 was identified to *Phoma* sp. according to the literature (Kobayashi, M. J. Antibact. Antifung. Agents 22, 757(1994)) and the like.

In addition, SANK 13899 strain was internationally deposited with the Agency of Industrial Science and Technology, Ministry of International Trade and Industry, at 1-3, Higashi 1-chome, Ibaraki-ken, Japan (International Patent Organism Depositary, National Institute of Advanced Industrial Science and Technology at AIST Tsukuba Central 6,1-1, Higashi 1-Chome, Tsukuba-shi, Ibaraki-ken, Japan), under the number of FERM BP-6851 dated Aug. 20, 1999.

It is well known to those skilled in the art that fungi are apt to be naturally and artificially (for example, by irradiation with UV, by irradiation with radioactivity, or by treatment with chemical reagents) mutated. SANK 13899 strain is also apt to be mutated. The present invention encompasses all such mutants. These mutants include ones prepared by genetic methods such as recombination, transduction, and transformation. SANK 13899 strain includes SANK 13899 strains producing F-15078 per se, mutants thereof and all fungi that cannot be distinguished from SANK 13899 strain.

Methods of Cultivation and Purification

As described above, the fermentation of a F-15078-producing strain is conducted in a culture medium, which is employed in order to produce general fermentation products. The culture medium contains carbon and nitrogen sources, inorganic salts, and trace amounts of growth factors and of metals, all of which can be utilized by microorganisms.

Examples of carbon sources include glucose, fructose, maltose, sucrose, mannitol, glycerin, dextrin, oatmeal, rye, corn starch, potato, corn powder, soy bean oil, cottonseed oil, syrup, citric acid and tartaric acid. These carbon sources can be used singly, or in combination of two or more than two of these.

The amount of the carbon source depends on which sources exist in the culture medium and so forth, but, however, is usually between 1 and 10% w/w.

Examples of nitrogen sources include soy bean powder, wheat bran, peanut powder, cottonseed powder, hydrolyzed product of casein, Pharmamin, corn steep liquor, peptone, meat extract, yeast, yeast extract, malt extract, sodium nitrate, ammonium nitrate, and ammonium sulfate. These nitrogen sources can be used singly, or in a combination of two or more than two of these.

The amount of the nitrogen source depends on the other components of the culture medium and so forth, but, however, is usually between 0.2 and 6% w/w.

It is not required to use high purity carbon or nitrogen sources, and they may contain trace amounts of growth factors, vitamins and inorganic nutrients. Certain salts that make ions such as sodium, potassium, magnesium, ammonium, calcium, phosphate, sulfate, chloride and carbonate, can be added into the culture medium.

In addition, vitamins such as vitamin B1 and biotin; thiamine which is a substance enhancing proliferation of the fungus; and metal salts such as manganate and molybdate; all of which the fungus can utilize, may be added to the culture medium.

When the culture medium is a solution, antifoaming agents such as silicon oils, polyalkylene glycol ethers, vegetable oils, animal oils and surfactants may also be added into the culture medium in order to prevent foaming.

The pH of the medium solution for the cultivation of the F-15078 producing microorganism depends upon the pH stability of F-15078 and of the producing strain; however, when SANK 13899 strain is employed, it is controlled between 5.0 and 7.0.

The temperature of the cultivation of the F-15078 producing microorganism depends upon the thermal stability of F-15078 and so forth; however, when said microorganism is SANK 13899 strain, it is between 15 and 37° C., preferably between 22 and 35° C., more preferably between 22 and 26° C. and most preferably 23° C.

There is no particular restriction in the method of fermentation of the F-15078 producing microorganism. Examples of fermentation methods include a cultivation using a solid culture medium, an agitating culture, a shaking culture, an aerating culture, and an aerating-agitating culture. Preferred methods are an agitating culture, a shaking culture, an aerating culture, and an aerating-agitating culture. A shaking culture is more preferred. The industrially preferred method is an aerating-agitating culture.

The first step of the fermentation of the F-15078 producing microorganism is a seed culture comprising inoculation of the said microorganism from a slant culture into a small volume of a culture medium and incubation thereof, followed by a large scale seed culture, if necessary. The substantial fermentation is carried out in a large volume of a culture medium in order to obtain the desired product.

When fermentation of the F-15078 producing microorganism is carried out on a small scale, the seed culture is conducted in an Erlenmeyer flask or the like followed, if necessary, by a large scale seed culture, and then a substantial cultivation is carried out, also in a Erlenmeyer flask or the like.

When fermentation of the F-15078 producing microorganism is carried out on a large scale, preferably a jar-fermentor or tank equipped with agitating and aerating apparatuses is used. It is possible for preparation of a culture medium and sterilization to be carried out in the jar-fermentor or tank-fermentor. The large scale production of F-15078 is preferably conducted in the same jar-fermentor or tank-fermentor.

The maximum production titer of F-15078 by SANK 13899 strain is obtained between 144 and 192 hours after the inoculation.

The F-15078 existing in the fermentation product can be extracted and purified by conventional techniques employing the physicochemical properties of F-15078 either from the fermentation product itself, from the filtrate which can be obtained by the filtration of the fermentation product with diatomaceous earth or the like, from the supernatant which can be obtained by the centrifugation of the fermentation product, and/or from the mycelium which can be obtained by said centrifugation or said filtration.

The F-15078 existing in the filtrate or the supernatant can be extracted under conditions of neutral pH by a solvent immiscible with water such as ethyl acetate, chloroform, ethylene chloride, methylene chloride, butanol, and mixtures of two or more than two thereof. The filtrate or the supernatant can be charged onto a column packed with activated charcoal, Amberlite XAD-2, Amberlite XAD-4 (products of Rohm and Haas Co.,Ltd,), Diaion HP-10, Diaion HP-20, Diaion CHP-20, Diaion HP-50, Sepabeads SP-207 (products of Mitsubishi Chemical Co.,Ltd.); and adsorbed F-15078 can be eluted with methanol-water, acetone-water, butanol-water or the like, or the other components which are adsorbed can be removed therefrom.

The F-15078 existing in the mycelium can be extracted with aqueous acetone or aqueous methanol, which contains 50 to 90% of organic solvent. The extract is filtered with diatomaceous earth and said organic solvent in the filtrate is removed. The F-15078 is purified from the concentrate by the same techniques as described for the filtrate or supernatant from the fermentation product.

The F-15078 existing in the fermentation product after cultivation can be extracted by the addition of the appropriate amount of acetone or methanol, preferably to a final concentration in the resulting mixture of 50% (volume/volume). The extract is filtered with diatomaceous earth and F-15078 is purified from the filtrate as described for the filtrate or supernatant from the fermentation product.

The desired product obtained above can be further purified by partition column chromatography using TSK gel Toyopearl HW-40F (product of Toso K.K.) or Sephadex LH-20 (Amersham Pharmacia Co.ltd); or reverse phase column chromatography using Cosmosil 140C18 (product of Nacalai Tesque K.K.). If necessary, the desired product isolated above can be further purified by high performance liquid chromatography (hereinafter referred to HPLC) using a reverse phase column such as Shodex Asahipak C8P50-4E (product of Showa Denko K.K.), YMCPak ODS-AM (product of YMC K.K.) and Capcellpak UG120 (product of Shiseido K.K.).

Isolation of F-15078 can be accomplished by a single extraction or purification technique as described above, or by appropriate combinations of individual extraction and purification techniques described above, and, if necessary, by repetition of the same extraction and purification techniques described above.

The progress of the fermentation of the F-15078 producing strain, and of the purification of F-15078A or F-15078B, can be monitored by the following methods 1 and 2.

1 Analytical Method Using HPLC

There is no particular restriction on HPLC methods provided that HPLC is used. For example, the following HPLC conditions can be applied.

Column: SHODEX ASAHIPAK C8P 50 4E (diameter 4.6 mm x 250 mm; product of Showa Denko K.K.)

Mobile phase: acetonitrile: 10 mM aqueous ammonium hydrogen carbonate=13:7

Flow rate: 0.7 ml/minute

Detection wave length: X 210 nm

Retention time of F-15078A: 10.20 minutes

Retention time of F-15078B: 9.05 minutes

2 Method by Measuring Antifungal Activity

There is no particular restriction on the method of evaluation of antifungal activity provided that evaluation of antifungal activity is used. For example, the broth dilution method described by Yamaguchi et al. (Yamaguchi, H. et al., J. Med. Mycol. 36, 61(12995)) can be applied.

Advantages of the Invention

The compounds (1) to (4) of this invention exhibit antifungal activity and are useful as therapeutic or prophylactic agents for fungal infectious diseases of human beings or of animals.

EXAMPLES

The following examples, test examples and formulation examples are intended to further illustrate the present invention and are not intended to limit the scope of this invention in any way.

Example 1

Preparation of F-15078A(1)

Cultivation of SANK 13899 Strain(1)

One loopful of the SANK 13899 strain was inoculated into previously sterilized (121° C., 30 minutes) pre-seed culture medium (100 ml) containing the ingredients shown in table 1 in each of three 500 ml Erlenmeyer flasks. The flasks were incubated at 23° C. for five days on a rotary shaker (210 rpm; 7 cm throw). 5% as a final concentration of the resulting pre-seed culture solution was inoculated into seed culture medium (400 ml) in each of nine 2 L Erlenmeyer flasks prepared in the same way as the pre-seed culture medium, and cultivated at 23° C. for two days on a rotary shaker (210 rpm; 7 cm throw). 5% as a final concentration of the resulting seed culture solution was inoculated into previously sterilized (121° C., 30 minutes) production culture medium (1) (1 5 L) containing the ingredients shown in table 2 in each of four 30 L jar-fermentors and incubated at 23° C. for seven days with agitation (from 100 to 420 rpm) and under aeration (aeration rate: 1 vvm, concentration of dissolved oxygen in the culture solution: 5.0 ppm).

TABLE 1

| Ingredients of pre-seed and seed culture medium | |
|---|---|
| Glycerin | 30 g |
| Glucose | 30 g |
| Soluble starch | 20 g |
| Soy bean powder | 10 g |
| Gelatin | 2.5 g |
| Yeast extract (Difco) | 2.5 g |
| $NH_4NO_3$ | 2.5 g |

TABLE 1-continued

Ingredients of pre-seed and seed culture medium

| | |
|---|---|
| Anti-foaming agent* | 0.1 ml |
| Tap water | 1000 ml |
| (pH was not adjusted) | |

*Nissan Disfoam CB-442 (product of Nihon Yushi K.K.)

TABLE 2

Ingredients of production culture medium (1)

| | |
|---|---|
| Dextrin (Difco) | 10 g |
| Glycerin | 20 g |
| Glucose | 30 g |
| Malt extract (Difco) | 10 g |
| Yeast extract (Difco) | 2 g |
| Tripton (Difco) | 1 g |
| $NH_4NO_3$ | 1 g |
| $NaNO_3$ | 1 g |
| $KH_2PO_4$ | 1 g |
| $MgSO_4 \cdot 7H_2O$ | 1 g |
| Anti-foaming agent* | 0.1 ml |
| Tap water | 1000 ml |
| (pH was not adjusted) | |

*Nissan Disfoam CB-442 (product of Nihon Yushi K.K.)

Isolation of F-15078A(1)

To the obtained culture solution (60 L) was added acetone (60 L) and then Celite 545(3 kg, product of Celite Corporation). The resulting suspension was subjected to filter-press filtration. The filtrate was partitioned with ethyl acetate (50 L). The extract (49 L) was washed with saturated aqueous sodium chloride (50 L) and water (50 L) and dried over anhydrous sodium sulfate (5 kg) for 1 hour and then was subjected to filter-press filtration to remove the sodium sulfate. The filtrate was concentrated in vacuo to dryness to afford an oil (95.9 g). The oil was dissolved in 100 ml of methanol:0.04% aqueous trifluoroacetic acid=8:2. This solution was charged onto a Toyopearl HW-40F column (product of Toso K.K., volume: 22 L) which was equilibrated with methanol:0.04% aqueous trifluoroacetic acid=8:2, and the column was developed with the same solvent. The eluate was collected in 500 ml fractions, and F-15078A was obtained from fractions 13 to 25 (total volume: 6:5 L). This eluate (6.5 L) was concentrated in vacuo to 2 L, adjusted to pH 7 with 6.25 N sodium hydroxide, and then the active substance was extracted with ethyl acetate (3.1 L). The extract was washed with saturated aqueous sodium chloride (3 L), dried over anhydrous sodium sulfate, and then concentrated in vacuo to dryness to afford an oil (66.5 g). The oil was dissolved in 160 ml of methanol:0.05% aqueous trifluoroacetic acid=8:2. This solution was charged on a Cosmocil 140C18 column (product of Nacalai Tesques K.K., volume: 3 L) which was equilibrated with acetonitrile:0.05% aqueous trifluoroacetic acid=4:6, and the column was washed with the same solvent (10 L) and then developed with acetonitrile:0.05% aqueous trifluoroacetic acid= 6:4. The eluate was collected in 2 L fractions, and F-15078A was obtained from the fraction number 2. This fraction (2 L) was concentrated in vacuo to 800 ml and adjusted to pH 7 with 6.25 N sodium hydroxide and then the active substance was extracted with ethyl acetate (1 L). The extract was washed and dried and then concentrated in vacuo to dryness to afford the crude desired product (234.3 mg). The crude product was subjected to HPLC under the conditions described below (1) to afford a fraction containing F-5078A.

Conditions of HPLC (1)

Column: YMC Pak ODS-AM diameter 30 mm×length 300 mm (product of YMC K.K.)

Solvent: Acetonitrile:aqueous triethylamine-phosphate (1%, pH 6.0)=3:1

Flow rate: 10.4 ml/minute

Temperature: Room temperature

Retention time: from 77 to 98 minutes

The fraction containing F-5078A was desalted by extraction with ethyl acetate as described above and concentrated in vacuo to dryness to give F-15078A (34.1 mg).

Example 2

Preparation of F-15078A (2)

Cultivation of SANK 13899 Strain (2)

One loopful of the strain SANK 13899 was inoculated into previously sterilized (121° C., 30 minutes) pre-seed culture medium (500 ml) containing the ingredients shown in table 1 in each of six 2 L Erlenmeyer flasks. The flasks were incubated at 23° C. for six days on a rotary shaker (210 rpm; 7 cm throw). 5% (v/v) as a final concentration of the resulting pre-seed culture solution was inoculated into previously sterilized (121° C., 30 minutes) seed culture medium (30 L) containing the ingredients shown in table 1 in each of two 60 L tank-fermentors and cultivated at 23° C. for two days with agitation (100 rpm) and under aeration (aeration ratio: 1 vvm, concentration of dissolved oxygen in the culture solution: 5.0 ppm). 5% (v/v) as a final concentration of the resulting seed culture solution was inoculated into previously sterilized (121° C., 30 minutes) production culture medium (2) (300 L) containing the ingredients shown in table 3 in a 600 L tank-fermentor and incubated at 23° C. for seven days with agitation (from 83 to 240 rpm) under aeration (aeration rate: 1 vvm, concentration of dissolved oxygen in the culture solution: 5.0 ppm).

TABLE 3

Ingredients of production culture medium (2)

| | |
|---|---|
| Glucose | 80 g |
| Malt extract (Difco) | 20 g |
| Yeast extract (Difco) | 2 g |
| Tripton (Difco) | 10 g |
| $NH_4NO_3$ | 1 g |
| $NaNO_3$ | 1 g |
| $KH_2PO_4$ | 1 g |
| $MgSO_4 \cdot 7H_2O$ | 1 g |
| Anti-foaming agent* | 0.1 ml |
| Tap water | 1000 ml |
| (pH was not adjusted) | |

*Nissan Disfoam CB-442 (product of Nihon Yushi K.K.)

Isolation of F-15078A (2)

To the obtained culture solution (370 L) was added Celite 545 (15 kg, product of Celite Corporation). The resulting mixture was subjected to filter-press filtration. Aqueous methanol (1:1, 400 L) was added to the mycelium cake, the suspension was stirred, and then the pH of the suspension was adjusted to 2 with 6N hydrochloric acid. The resulting suspension was subjected to filter-press filtration. The total volume of the combined filtrate was 465 L. A 270-L portion of filtrate was charged onto a Cosmocil 140 C18-OPN column (product of Nacalai Tesque K.K., volume: 30 L) which was equilibrated with methanol:0.05% aqueous trifluoroacetic acid=1:1. The column was washed with the same solvent (270 L) and acetonitrile:0.05% aqueous trifluoroacetic acid=4:6 (100 L), and then developed with acetonitrile:0.05% aqueous trifluoroacetic acid=6:4. The eluant was collected as a first fraction (fraction 1; 15 liters) and then five further fractions (fractions 2 to 6; 10 liters each), and F-15078A was eluted in fractions 2 to 4 (30 liters).

The rest of the filtrate (195 L) obtained above was charged onto a Cosmocil 140 C18-OPN column (product of Nacalai Tesque K.K., volume 30 L), which was equilibrated with methanol:0.05% aqueous trifluoroacetic acid=1:1. The column was washed with the same solvent (200 L) and acetonitrile:0.05% aqueous trifluoroacetic acid=4:6 (100 L), and then developed with acetonitrile:0.05% aqueous trifluoroacetic acid=6:4. The eluant was collected as a first fraction (10 L), a second fraction (5 L), two further fractions (fractions 3 and 4; 15 L each), and a fifth fraction (10 L), and F-15078A was eluted in fractions 3 to 5 (total 40 L).

The combined fractions (total 70 L) containing F-15078A obtained from the two trials above were adjusted to pH 7 with 6N sodium hydroxide and then the active substance was extracted with ethyl acetate (50 L). The extract was washed with saturated aqueous sodium chloride, dried over anhydrous sodium sulfate, and then concentrated in vacuo to dryness to afford an oil (32.3 g).

The oil was dissolved in methanol (200 ml). 50 ml of the solution was subjected to HPLC under the following conditions (2), and the residual 150 ml of methanol solution was divided into five portions and each portion (30 ml) was subjected to HPLC under conditions (2) to afford a combined fraction (26 L) containing F-15078A. Water (10 L) was added to the combined fraction, F-15078A was extracted with ethyl acetate (10 L), and the extract was washed, dried and concentrated in vacuo to dryness to afford the crude product (7.78 g). A solution of a 326 mg portion of the crude product in methanol (2 ml) was divided into ten portions (each portion is 200 μl). Each portion was subjected to HPLC under the following conditions (3), and the fractions containing the desired product were combined, concentrated and lyophilized to give F-15078A (275 mg).

Conditions of HPLC (2)
  Column: YMC Pak ODS-AM diameter 100 mm×length 500 mm (product of YMC K.K.)
  Solvent: Acetonitrile:aqueous triethylamine-phosphate (1%, pH 6.0)=3:1
  Detection wave length: UV 210 nm
  Flow rate: 240 ml/minute
  Temperature: Room temperature
  Retention time: 64 minutes
Conditions of HPLC (3)
  Column: SHODEX ASAHIPAK C8P 90 2F diameter 20 mm×length 250 mm (product of Showa Denko K.K.)
  Solvent: Acetonitrile: 10 mM aqueous ammonium hydrogencarbonate=6:4
  Detection wave length: UV 210 nm
  Flow rate: 14 ml/minute
  Temperature: Room temperature
  Retention time: 19.2 minutes Example 3

Preparation of F-15078B

Cultivation of SANK 13899 Strain (3)

One loopful of the strain SANK 13899 was inoculated into previously sterilized (121° C., 30 minutes) pre-seed culture medium (500 ml) containing the ingredients shown in table 1 in each of six 2 L Erlenmeyer flasks. The flasks were incubated at 23° C. for six days on a rotary shaker (210 rpm, 7 cm throw). 5% (v/v) as a final concentration of the resulting pre-seed culture solution was inoculated into previously sterilized (121° C., 30 minutes) seed culture medium (30 L) containing the ingredients shown in Table 1 in each of two 60 L tank-fermentors and cultivated at 23° C. for two days with agitation (100 rpm) and under aeration (aeration ratio: 1 vvm, concentration of dissolved oxygen in the culture solution: 5.0 ppm). 5% (v/v) as a final concentration of the resulting seed culture solution was inoculated into previously sterilized (121° C., 30 minutes) production culture medium (2) (300 L) containing the ingredients shown in table 3 of Example 2 in a 600-L tank-fermentor and incubated at 23° C. for seven days with agitation (from 83 to 240 rpm) and under aeration (aeration rate: 1 vvm, concentration of dissolved oxygen in the culture solution: 5.0 ppm).

Isolation of F-15078B

To the culture solution (370 L) was added Celite 545 (15 kg, product of Celite Corporation). The resulting suspension was subjected to filter-press filtration. Aqueous methanol (1:1, 400 L) was added to the mycelial cake, the suspension was stirred, and then the pH of the suspension was adjusted to 2 with 6N hydrochloric acid. The resulting suspension was subjected to filter-press filtration. The total volume of the combined filtrate was 465 L. A 270 L portion of the filtrate was charged onto a Cosmocil 140 C18-OPN column (product of Nacalai Tesque K.K., volume: 30 L) which was equilibrated with methanol:0.05% aqueous trifluoroacetic acid=1:1. The column was washed with the same solvent (270 L) and acetonitrile:0.05% aqueous trifluoroacetic acid= 4:6 (100 L), and then developed with acetonitrile:0.05% aqueous trifluoroacetic acid=6:4. The eluant was collected as a first fraction (fraction 1; 15 liters) and then five further fractions (fractions 2 to 6; 10 liters each), and F-15078B was eluted in fractions 2 to 4 (30 liters).

The rest of the filtrate (195 L) obtained above was charged onto a Cosmocil 140 C18-OPN column (product of Nacalai Tesque K.K., volume 30 L), which was equilibrated with methanol:0.05% aqueous trifluoroacetic acid=1:1. The column was washed with the same solvent (200 L) and acetonitrile:0.05% aqueous trifluoroacetic acid=4:6 (100 L), and then developed with acetonitrile:0.05% aqueous trifluoroacetic acid=6:4. The eluant was collected as a first fraction (10 L), a second fraction (5 L), two further fractions (fractions 3 and 4; 15 L each), and a fifth fraction (10 L), and F-15078B was eluted in fractions 3 to 5 (total 40 L).

The combined fractions (total 70 L) containing F-15078B obtained from the two trials above were adjusted to pH 7 with 6N sodium hydroxide and then the active substance was extracted with ethyl acetate (50 L). The extract was washed with saturated aqueous sodium chloride (50 L), dried over anhydrous sodium sulfate, and then concentrated in vacuo to dryness to afford an oil (32.3 g). The oil was dissolved in methanol (200 ml). 50 ml of the solution was subjected to HPLC under conditions (2) of Example 2, and the residual 150 ml of methanol solution was divided into five portions and each portion (30 ml) was subjected to HPLC under conditions (2) of Example 2 to afford a combined fraction (26 L) containing F-15078B. Water (10 L) was added to the resulting fraction, the active substance was extracted with ethyl acetate (10 L), and the extract was washed, dried and concentrated in vacuo to dryness to afford the crude product (7.78 g).

To a solution of the crude product (2.10 g) in methanol (5 ml) was added Cosmocil 140C18-OPN (5 g, product of Nacalai Tesque K.K.) and then the solvent was removed by evaporation. The residue was embedded on a Cosmocil 140C18-OPN column (volume: 170 ml) which was equilibrated with acetonitrile: 0.05% aqueous trifluoroacetic acid= 4:6. After washing with the same solvent (300 ml), the column was developed with acetonitrile: 0.05% aqueous trifluoroacetic acid=6:4 (300 ml) and then further developed with acetonitrile: 0.05% aqueous trifluoroacetic acid=9:1. The eluate was collected in 10 ml fractions, and F-15078B was eluted in fractions 64 to 72 (total 90 ml). These fractions were combined, concentrated in vacuo, and lyophilized to afford a yellowish white powder (109 mg). A solution of the powder (100 mg) in methanol (1 ml) was divided into five portions (each portion is 200 μl). Each portion was subjected to HPLC under the following conditions (4), and the fractions containing the desired product were combined, concentrated and lyophilized to give F-15078B (69.5 mg) as a white powder.

Conditions of HPLC (4)

Column: SHODEX ASAHIPAX C8P 90 2F diameter 20 mm×length 250 mm (product of Showa Denko K.K.)

Solvent: Acetonitrile: 10 mM aqueous ammonium hydrogencarbonate=6:4

Detection wave length: UV 210 nm

Flow rate: 14 ml/minute

Temperature: Room temperature

Retention time: 17.8 minutes

Test Example 1

Antifungal Activity of F-15078A and F-15078B

The antifungal activity of F-15078A and F-5078B, that is, the minimum inhibitory concentration (MIC) of the compounds against each test strain, was determined by the broth dilution method (Yamaguchi,H., et al., J. Med. Mycol. 36, 61(1995)) on a microtiterplate with 96 wells using RPMI 1640 culture medium containing 0.165 M 3-[N-morpholino]propanesulfonic acid (product of Sigma Company) buffer solution. The results are shown in Table 4.

TABLE 4

Antifungal activity of F-15078A and F-15078B

| Test strain | MIC (μg/ml) | |
|---|---|---|
| | F-15078A | F-15078B |
| Candida albicans ATCC 90028 | 2.5 | >50 |
| Aspergillus fumigatus IAM 2034 | 1.3 | >50 |
| Cryptococcus neoformans IAM 4772 | 0.31 | 1.56 |

As shown in Table 4, F-15078A and F-15078B exhibited antifungal activity.

Formulation Example 1

Capsule for Oral Administration

| | |
|---|---|
| F-15078A | 30 mg |
| Lactose | 170 mg |
| Corn starch | 150 mg |
| Magnesium stearate | 2 mg |
| Total | 352 mg |

The ingredients listed above in powder form are mixed and passed through a 30 mesh sieve. The resulting powder mixture is placed into a gelatin capsule to afford the desired capsule.

Possibility for Industrial Use

The compounds of the present invention exhibit antifungal activity and are useful in the treatment or prevention of fungal infectious diseases.

When the compounds of this invention are used as a therapeutic or prophylactic agent for fungal infectious diseases, there is no limitation with respect to the administration route, and it can be appropriately selected depending upon the formulation, and the age, sex, disease and symptoms of the patient and so forth.

Tablets, pills, powders, granules, syrups, solutions, suspensions, emulsions, and capsules can be orally administered. The active ingredient alone, a solution containing the active ingredient, glucose and amino acid and the like, or an emulsion containing the active ingredient, polyoxyethylene sorbitan esters of fatty acids and the like can be injected intravenously, intramuscularly, subcutaneously, intracutaneously and/or intraperitonealy. Suppositories can be administered into the rectum.

These formulations can be prepared using an active ingredient and adjuvants or carriers known to those skilled in the art such as excipients, binders, disintegrants, lubricants, solvents, corrigents and coating agents.

Carriers known to those skilled in the art for preparation of tablets include excipients such as lactose, sucrose, sodium chloride, glucose, urea, starch, calcium carbonate, kaolin, crystalline cellulose, and silicic acid; binders such as water, ethanol, propanol, simple syrup, solutions of glucose, solutions of starch, solutions of gelatin, carboxymethyl cellulose, shellac, methyl cellulose, potassium phosphate, and polyvinylpyrrolidone; disintegrants such as dried starch, sodium alginate, agar powder, laminaran powder, sodium hydrogencarbonate, calcium carbonate, polyoxyethylene sorbitan esters of fatty acids, sodium lauryl sulfate, stearic acid mono-glyceride, starch and lactose; disintegration suppressants such as sucrose, stearin, cacao butter, and hydrogenated oil; absorption facilitators such as quaternary ammonium base, and sodium lauryl sulfate; humectants such as glycerin and starch; adsorbents such as starch, lactose, kaolin, bentonite, and colloidal silicic acid; and lubricants such as purified talc, stearates, boric acid powder, and polyethylene glycol. If necessary, the tablets can be converted into coated tablets such as sugar coated tablets, gelatin coated tablets, enteric coated tablets, film coated tablets, double coated tablets and multiple coated tablets.

Carriers for preparation of pills are those known to those skilled in the art. Examples of such carriers include excipients such as glucose, lactose, starch, cacao butter, hydrogenated vegetable oil, kaolin, and talc; binders such as acacia powder, tragacanth powder, gelatin, and ethanol; disintegrants such as laminaran, and agar; and the like.

Carriers for preparation of suppositories are those known to those skilled in the art. Examples of such carriers include polyethylene glycol, cacao butter, higher alcohols, esters of higher alcohols, gelatin, and semi-synthetic glycerides.

When the formulation for injection is a solution, emulsion or suspension, the formulations are preferably sterilized and isotonic to the blood. Diluents for preparation of solutions, emulsions and suspensions for injection are those known to those skilled in the art. Examples of such diluents include water, ethyl alcohol, propylene glycol, epoxidized isostearyl alcohol, polyoxidized isostearyl alcohol, polyoxyethylene sorbitan esters of fatty acids and the like. The injection formulations may contain a sufficient amount of salt, glucose, glycerin and the like in order to make the solution, emulsion or suspension isotonic to the blood, and may also contain an adjuvant such as a solubilization agent, buffering agent, soothing agent or the like.

These formulations can contain, if necessary, a coloring agent, preservative, flavoring agent, sweetening agent, or the like.

The amount of the active ingredient of this invention in a dosage form depends on the formulation, the administration route and so on; it is from 1 to 70% by weight of the dosage form, and preferably from 1 to 30%. The dose of the compound of this invention depends on a variety of factors such as the disease, symptoms, age, and body weight of the patient, the administration route, the formulation and so on. A suitable dosage level is from 20 to 2000 mg as an upper limit per day for a human adult and is from 0.001 to 0.1 mg as a lower limit per day for a human adult. The preferred dosage level is from 0.01 mg to 200 mg and more preferably from 0.1 to 20 mg.

A medicament containing the compound of this invention can be administered either as a single unit dosage per several days or the dosage may be divided into convenient sub-units administered from one to several times throughout the day depending on the formulation, and disease, symptoms and body weight of the patient (human or non-human animal) and so forth.

The following is a list of fungal diseases that the compounds of the present invention can be administered for treating and/or preventing:

1. Deepseated mycosis/systemic mycosis such as:
   aspergillosis, candidiasis, histoplasmosis, blastomycosis, cryptococcosis, mucormycosis, coccidioidomycosis and paracoccidioidomycosis.
2. Superficial mycosis such as the following:
   favus, trichophytia, oral moniliasis, otomycosis, dermatomycosis and cutaneous candidiasis.
3. Subcutaneous mycosis such as the following:
   chromomycosis, sporotrichosis, maduromycosis and keratomycosis.

What is claimed is:

1. A compound of the following chemical structure (I), or a pharmaceutically acceptable salt thereof:

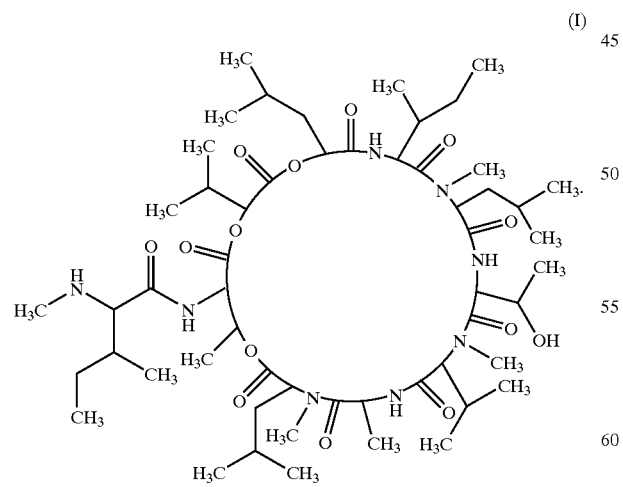

(I)

2. A compound having the following physicochemical properties, or a pharmaceutically acceptable salt thereof:
   1) Property: Basic liposoluble powder
   2) Molecular formula C55H98N8O14

3) Molecular weight: 1094 (FAB-MS method)
4) High resolution FAB-MS [M+H]$^+$
   calculated for $C_{55}H_{99}N_8O_{14}$ 1095.7281
   found 1095.7365
5) Ultra violet absorption spectrum: End absorption
6) Infra red absorption spectrum (KBr pellet, cm$^{-1}$) 3434, 3335, 2962, 2937, 2875, 2806, 1750, 1684, 1641, 1509, 1469, 1412, 1371, 1314, 1294, 1271, 1204, 1156, 1128, 1074, 1020
7) Optical rotation: $[\alpha]_D^{25}$ –120° (c 1.0, methanol)
8) $^1$H NMR spectrum (in CDCl$_3$, 500 MHz, δ(ppm), internal standard:
   tetramethylsilane): 0.78(3H), 0.79(3H), 0.80(3H), 0.82 (3H), 0.87(3H), 0.88(1H), 0.92(3H), 0.93(3H), 0.94 (3H), 0.96(3H), 0.97(3H), 0.98(3H), 1.01(3H), 1.02 (3H), 1.03(3H), 1.06(3H), 1.21(1H), 1.41(3H), 1.41 (1H), 1.48(1H), 1.48(1H), 1.49(1H), 1.52(3H), 1.55 (1H), 1.65(1H), 1.66(1H), 1.70(2H), 1.73(1H), 1.81 (1H), 1.87(1H), 2.28(1H), 2.31(1H), 2.37(1H), 2.48 (3H), 2.89(3H), 2.94(3H), 2.96(1H), 3.29(3H), 3.56 (1H), 4.06(1H), 4.14(1H), 4.77(1H), 4.78(1H), 4.84 (1H), 4.91(1H), 4.96(1H), 5.21(1H), 5.25(1H), 5.53 (1H), 6.39(1H), 7.83(1H), 7.94(1H), 8.28(1H)
9) $^{13}$C NMR spectrum (in CDCl$_3$, 500 MHz, δ (ppm), internal
   standard: tetramethylsilane): 10.9(q), 11.9(q), 15.0(q), 15.1(q), 16.0(q), 16.6(q), 17.4(q), 18.3(q), 18.6(q), 18.7(q), 19.1(q), 21.0(q), 21.4(q), 22.1(q), 23.1(q), 23.51(q), 23.54(q), 24.2(t), 24.6(d), 24.8(d), 25.4(d), 25.5(t), 27.7(d), 29.5(q), 29.8(d), 30.2(q), 36.1(q), 36.5(t), 37.7(t), 38.3(d), 38.4(d), 39.7(t), 40.9(q), 46.2(d), 51.8(d), 53.1(d), 54.7(d), 55.1(d), 63.9(d), 64.7(d), 68.1(d), 70.1(d), 73.4(d), 74.3(d), 77.1(d), 169.03(s), 169.04(s), 169.6(s), 169.8(s), 169.9(s), 170.3(s), 172.0(s), 173.4(s), 173.8(s), 174.0(s)
10) Solubility: soluble in dimethylsulfoxide, methanol, and chloroform
11) Amino acid analysis: Threonine, alanine and isoleucine were detected from the hydrolysate.

3. A compound of the following chemical structure (II):

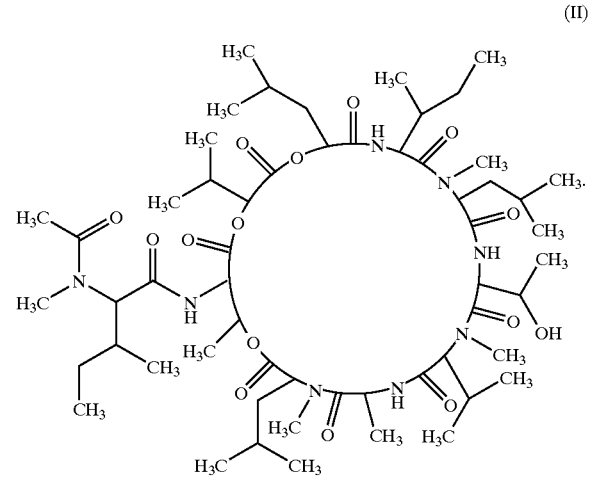

(II)

4. A compound having the following physicochemical properties:
   1) Property: Neutral liposoluble powder
   2) Molecular formula: $C_{57}H_{100}N_8O_{15}$
   3) Molecular weight: 1136 (FAB-MS method)

4) High resolution FAB-MS [M+H]$^+$
   calculated for $C_{57}H_{101}N_8O_{15}$ 1137.7387
   found 1137.7410
5) Ultra violet absorption spectrum: End absorption
6) Infra red absorption spectrum (KBr pellet, cm$^{-1}$) 3433, 3333, 2963, 2937, 2875, 1751, 1686, 1642, 1516, 1469, 1409, 1388, 1372, 1311, 1292, 1272, 1201, 1156, 1128, 1074, 1017
7) Optical rotation: $[\alpha]_D^{25}$ –131° (c 1.0, methanol)
8) $^1$NMR spectrum (in CDCl$_3$, 500 MHz, δ (ppm), internal standard: tetramethylsilane): 0.78(3H), 0.79 (3H), 0.80(3H), 0.83(3H), 0.87(1H), 0.87(3H), 0.90 (3H), 0.92(3H), 0.93(3H), 0.95(3H), 0.95(3H), 0.98 (3H), 0.98(3H), 1.01(3H), 1.01(3H), 1.03(1H), 1.05 (3H), 1.28(3H), 1.37(1H), 1.40(1H), 1.46(1H), 1.47 (1H), 1.49(1H), 1.51(3H), 1.64(1H), 1.65(1H), 1.66 (1H), 1.86(1H), 1.72(1H), 1.78(1H), 2.12(3H), 2.13 (1H), 2.26(1H), 2.31(1H), 2.37(1H), 2.88(3H), 2.93 (3S), 2.97(3H), 3.28(3H), 3.56(1H), 4.03(1H), 4.15 (1H), 4.73(1H), 4.78(1H), 4.82(1H), 4.83(1H), 4.91 (1H), 4.97(1H), 5.15(1H), 5.28(1H), 5.50(1H), 6.37 (1H), 6.87(1H), 7.86(1H), 8.29(1H)
9) $^{13}$C NMR spectrum (in CDCl$_3$, 500 MHz, δ (ppm), internal standard: tetramethylsilane): 10.5(q), 10.9(q), 14.9(q), 15.1(q), 15.6(q), 16.6(q), 16.7(q), 18.3(q), 18.6 (q), 18.7(q), 19.0(q), 20.8(q), 21.4(q), 22.0(q), 22.1(q), 23.1(q), 23.6(q), 23.6(q), 24.1(t), 24.6(t), 24.7(d), 24.8 (d), 25.4(d), 27.7(d), 29.5(q), 29.8(d), 30.2(q), 31.6(d), 31.8(q), 36.1(t), 37.6(t), 38.4(d), 39.6(t), 40.9(q), 46.1 (d), 51.8(d), 53.1(d), 54.7(d), 54.7(d), 61.2(d), 63.9(d), 64.6(d), 68.1(d), 73.1(d), 74.3(d), 77.0(d), 168.9(s), 168.9(s), 169.1(s), 169.9(s), 169.9(s), 170.3(s), 170.6 (s), 171.7(s), 172.0(s), 173.3(s), 173.8(s)
10) Solubility: Soluble in dimethylsulfoxide, methanol, and chloroform
11) Amino acid analysis: Threonine, alanine and isoleucine were detected from the hydrolysate.

5. A process for preparing the compound according to claim 1, comprising fermenting a microorganism which is *Phoma* sp. SANK 13899 (FERM BP-6851) strain, and produces the compound according to claim 1, and isolating the compound according to claim 1 from the fermentation product of said microorganism.

6. A process for preparing the compound according to claim 2, comprising fermenting a microorganism which is *Phoma* sp. SANK 13899 (FERM BP-6851) strain, and produces the compound according to claim 2, and isolating the compound according to claim 2 from the fermentation product of said microorganism.

7. A process for preparing the compound according to claim 3, comprising fermenting a microorganism which is *Phoma* sp. SANK 13899 (FERM BP-6851) strain, and produces the compound according to claim 3, and isolating the compound according to claim 3 from the fermentation product of said microorganism.

8. A process for preparing the compound according to claim 4, comprising fermenting a microorganism which is *Phoma* sp. SANK 13899 (FERM BP-6851) strain, and produces the compound according to claim 4, and isolating the compound according to claim 4 from the fermentation product of said microorganism.

9. A fungicidal composition comprising a fungicidally effective amount of the compound according to claim 1 as an active ingredient in combination with a pharmaceutically acceptable carrier.

10. A fungicidal composition comprising a fungicidally effective amount of the compound according to claim 2 as an active ingredient in combination with a pharmaceutically acceptable carrier.

11. A fungicidal composition comprising a fungicidally effective amount of the compound according to claim 3 as an active ingredient in combination with a pharmaceutically acceptable carrier.

12. A fungicidal composition comprising a fungicidally effective amount of the compound according to claim 4 as an active ingredient in combination with a pharmaceutically acceptable carrier.

13. A method for treating an infectious fungal disease, which comprises administering a pharmaceutically effective amount of the compound according to claim 1 to a human or a non-human animal, wherein the infectious fungal disease is at least one disease selected from the group consisting of (i) a deepseated mycosis and a systemic mycosis, which is selected from the group consisting of *aspergillosis, cryptococcosis* and *candidiasis*, and (ii) a superficial mycosis of *candidiasis*.

14. The method of claim 13, wherein the compound is administered to a human.

15. A method for treating an infectious fungal disease, which comprises administering a pharmaceutically effective amount of the compound according to claim 2 to a human or a non-human animal, wherein the infectious fungal disease is at least one disease selected from the group consisting of (i) a deepseated mycosis and a systemic mycosis, which is selected from the group consisting of *aspergillosis, cryptococcosis* and *candidiasis*, and (ii) a superficial mycosis of *candidiasis*.

16. The method of claim 15, wherein the compound is administered to a human.

17. A method for treating an infectious fungal disease, which comprises administering a pharmaceutically effective amount of the compound according to claim 3 to a human or a non-human animal, wherein the infectious fungal disease is at least one disease selected from the group consisting of a deepseated mycosis and a systemic mycosis, which is *cryptococcosis*.

18. The method of claim 17, wherein the compound is administered to a human.

19. A method for treating an infectious fungal disease, which comprises administering a pharmaceutically effective amount of the compound according to claim 4 to a human or a non-human animal, wherein the infectious fungal disease is at least one disease selected from the group consisting of a deepseated mycosis and a systemic mycosis, which is *cryptococcosis*.

20. The method of claim 19, wherein the compound is administered to a human.

21. A compound having the following physicochemical properties or a salt thereof:
   1) property: basic and liposoluble powder
   2) ultra violet absorption spectrum: end absorption
   3) $^1$H-NMR (in CDCl$_3$, 500 MHz, δ ppm, internal standard: tetramethylsilane):
      0.78(3H), 0.79(3H), 0.80(3H), 0.82(3H), 0.87(3H), 0.88(1H), 0.92(3H), 0.93(3H), 0.94(3H), 0.96(3H), 0.97(3H), 0.98(3H), 1.01(3H), 1.02(3H), 1.03(3H), 1.06(3H), 1.21(1H), 1.41(3H), 1.41(1H), 1.48(1H), 1.48(1H), 1.49(1H), 1.52(3H), 1.55(1H), 1.65(1H), 1.66(1H), 1.70(2H), 1.73(1H), 1.81(1H), 1.87(1H), 2.29(1H), 2.31(1H), 2.37(1H), 2.48(3H), 2.89(3H), 2.94(3H), 2.96(1H), 3.29(3H), 3.56(1H), 4.06(1H), 4.14(1H), 4.77(1H), 4.78(1H), 4.84(1H), 4.91(1H), 4.96(1H), 5.21(1H), 5.25(1H), 5.53(1H), 6.39(1H), 7.83(1H), 7.94(1H), 8.28(1H)

4) $^{13}$C NMR spectrum (in CDCl$_3$, 500 MHz, δ ppm, internal standard: tetramethylsilane): 10.9(q), 11.9(q), 15.0(q), 15.1(q), 16.0(q), 16.6(q), 17.4(q), 18.3(q), 18.6(q), 18.7(q), 19.1(q), 21.0(q), 21.4(q), 22.1(q), 23.1(q), 23.51(q), 23.54(q), 24.2(t), 24.6(d), 24.8(d), 25.4(d), 25.5(t), 27.7(d), 29.5(q), 29.8(d), 30.2(q), 36.1(q), 36.5(t), 37.7(t), 38.3(d), 38.4(d), 39.7(t), 40.9(q), 46.2(d), 51.8(d), 53.1(d), 54.7(d), 55.1(d), 63.9(d), 64.7(d), 68.1(d), 70.1(d), 73.4(d), 74.3(d), 77.1(d), 169.03(s), 169.04(s), 169.6(s), 169.8(s), 169.9(s), 170.3(s), 172.0(s), 173.4(s), 173.8(s), 174.0(s)

5) solubility: soluble in dimethylsulfoxide, methanol, and chloroform 6) amino acid analysis: hydrolysis products are threonine, alanine and isoleucine.

22. A process for preparing the compound of claim 21 comprises isolation of the compound from an incubation product of a microorganism that is *Phoma* sp. SANK 13899 (FERM BP-6851) strain and which produces the compound.

23. The method of claim 13, wherein the fungal disease is selected from the group consisting of a deepseated mycosis and a systemic mycosis, which is selected from the group consisting of *aspergillosis, cryptococcosis* and *candidiasis*.

24. The method of claim 15, wherein the fungal disease is selected from the group consisting of a deepseated mycosis and a systemic mycosis, which is selected from the group consisting of *aspergillosis, cryptococcosis* and *candidiasis*.

25. The method of claim 13 wherein the fungal disease is caused by *Candida albicans*.

26. The method of claim 13, wherein the fungal disease is caused by *Aspergillus fumigatus*.

27. The method of claim 13, wherein the fungal disease is caused by *Cryptococcus neoformans*.

28. The method of claim 15, wherein the fungal disease is caused by *Candida alibcans*.

29. The method of claim 15, wherein the fungal disease is caused by *Aspergillus fumigatus*.

30. The method of claim 15, wherein the fungal disease is caused by *Cryptococcus neoformans*.

31. The method of claim 17, wherein the fungal disease is caused by *Cryptococcus neoformans*.

32. The method of claim 19, wherein the fungal disease is caused by *Cryptococcus neoformans*.

* * * * *

UNITED STATES PATENT AND TRADEMARK OFFICE
CERTIFICATE OF CORRECTION

PATENT NO.   : 6,818,614 B2
DATED        : November 16, 2004
INVENTOR(S)  : Yano et al.

It is certified that error appears in the above-identified patent and that said Letters Patent is hereby corrected as shown below:

Column 7,
Line 16, insert the following paragraph:
-- SANK 13899 strain does not grow on G25N medium. --.

Column 21,
Line 17, before "comprises" insert -- which --.

Signed and Sealed this

Twenty-first Day of March, 2006

JON W. DUDAS
*Director of the United States Patent and Trademark Office*